United States Patent
Chernov et al.

(10) Patent No.: US 9,844,384 B2
(45) Date of Patent: Dec. 19, 2017

(54) STAND ALONE ENERGY-BASED TISSUE CLIPS

(75) Inventors: Boris Chernov, Saint-Petersburg (RU); Nataliya Chernova, legal representative, Saint-Petersburg (RU); Igoris Misuchenko, Saint-Petersburg (RU); Georgy Martsinovskiy, Saint-Petersburg (RU); Mikhail Verbitsky, Stoughton, MA (US)

(73) Assignee: COVIDIEN LP, Mansfield, MA (US)

(*) Notice: Subject to any disclaimer, the term of this patent is extended or adjusted under 35 U.S.C. 154(b) by 371 days.

(21) Appl. No.: 13/179,960

(22) Filed: Jul. 11, 2011

(65) Prior Publication Data

US 2013/0018364 A1 Jan. 17, 2013

(51) Int. Cl.
*A61B 18/18* (2006.01)
*A61B 17/122* (2006.01)
*A61B 18/14* (2006.01)
*A61B 5/05* (2006.01)
*A61B 18/20* (2006.01)
(Continued)

(52) U.S. Cl.
CPC ........ *A61B 17/122* (2013.01); *A61B 18/1442* (2013.01); *A61B 5/05* (2013.01); *A61B 18/20* (2013.01); *A61B 2017/00004* (2013.01); *A61B 2017/00026* (2013.01); *A61B 2017/00119* (2013.01); *A61B 2017/00199* (2013.01); *A61B 2017/00221* (2013.01); *A61B 2017/00517* (2013.01); *A61B 2017/00734* (2013.01); *A61B 2017/00867* (2013.01); *A61B 2018/0063* (2013.01); *A61B 2018/00273* (2013.01); *A61B 2018/00428* (2013.01); *A61B 2018/00607* (2013.01); *A61B 2018/00642* (2013.01); *A61B 2018/00702* (2013.01); *A61B 2018/00779* (2013.01); *A61B 2018/00875* (2013.01); *A61B 2018/1226* (2013.01); *A61B 2090/065* (2016.02)

(58) Field of Classification Search
CPC ................ A61B 18/1206; A61B 18/12; A61B 2018/0066; A61B 2018/00607; A61B 2018/00642
USPC ............................................... 606/37, 45–52
See application file for complete search history.

(56) References Cited

U.S. PATENT DOCUMENTS

| 2,245,030 A | 6/1941 | Gottesfeld et al. |
| D249,549 S | 9/1978 | Pike |

(Continued)

FOREIGN PATENT DOCUMENTS

| CN | 201299462 | 9/2009 |
| DE | 2415263 | 10/1975 |

(Continued)

OTHER PUBLICATIONS

U.S. Appl. No. 08/926,869, filed Sep. 10, 1997, James G. Chandler.
(Continued)

*Primary Examiner* — John R Downey

(57) ABSTRACT

The present disclosure is directed to a tissue clip for use in electrosurgical procedures. The tissue clip includes an arm having a first electrode formed thereon. The tissue clip also includes a body pivotally coupled to the arm. The body includes a power source and a second electrode. The arm is moveable from a first position relative to the body for approximating tissue and a second position closer to the body for grasping tissue therebetween.

19 Claims, 13 Drawing Sheets

(51) Int. Cl.
  *A61B 17/00* (2006.01)
  *A61B 18/00* (2006.01)
  *A61B 18/12* (2006.01)
  *A61B 90/00* (2016.01)

(56) References Cited

U.S. PATENT DOCUMENTS

| | | | |
|---|---|---|---|
| D263,020 S | 2/1982 | Rau, III | |
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| 5,201,900 A | 4/1993 | Nardella | |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| D384,413 S | 9/1997 | Zlock et al. | |
| H1745 H | 8/1998 | Paraschac | |
| D402,028 S | 12/1998 | Grimm et al. | |
| D408,018 S | 4/1999 | McNaughton | |
| 5,891,142 A * | 4/1999 | Eggers et al. | 606/51 |
| D416,089 S | 11/1999 | Barton et al. | |
| D424,694 S | 5/2000 | Tetzlaff et al. | |
| D425,201 S | 5/2000 | Tetzlaff et al. | |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| 6,514,250 B1 * | 2/2003 | Jahns et al. | 606/41 |
| 6,682,527 B2 * | 1/2004 | Strul | 606/51 |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| 7,114,502 B2 | 10/2006 | Schulman et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 8,162,940 B2 * | 4/2012 | Johnson et al. | 606/51 |
| 8,177,783 B2 * | 5/2012 | Davison et al. | 606/37 |
| 8,491,624 B2 * | 7/2013 | Kerr | A61B 17/29 606/205 |
| 2002/0165541 A1 * | 11/2002 | Whitman | 606/48 |
| 2005/0021020 A1 * | 1/2005 | Blaha | A61B 18/1233 606/34 |
| 2006/0206110 A1 * | 9/2006 | Knowlton et al. | 606/41 |
| 2007/0123854 A1 * | 5/2007 | Clague et al. | 606/45 |
| 2007/0173811 A1 | 7/2007 | Couture et al. | |
| 2007/0208339 A1 * | 9/2007 | Arts | A61B 17/32056 606/47 |
| 2009/0138006 A1 * | 5/2009 | Bales | A61B 18/1206 606/33 |
| 2009/0261804 A1 * | 10/2009 | McKenna et al. | 324/71.1 |
| 2010/0057084 A1 * | 3/2010 | Hanna | 606/51 |
| 2010/0211080 A1 | 8/2010 | Trivisani et al. | |
| 2010/0292691 A1 * | 11/2010 | Brogna | 606/45 |
| 2011/0270250 A1 * | 11/2011 | Horner et al. | 606/49 |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026179 | 12/2005 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 0986990 A1 | 3/2000 |
| EP | 1159926 | 12/2001 |
| EP | 2158867 A1 | 3/2010 |
| JP | 61-501068 | 9/1984 |
| JP | 6-502328 | 3/1992 |
| JP | 5-5106 | 1/1993 |
| JP | 5-40112 | 2/1993 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-252263 | 10/1996 |
| JP | 8-317934 | 12/1996 |
| JP | 9-10223 | 1/1997 |
| JP | 9-122138 | 5/1997 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2004-517668 | 6/2004 |
| JP | 2004-528869 | 9/2004 |
| JP | 2007-282666 A | 11/2007 |
| SU | 401367 | 11/1974 |
| WO | WO 00/36986 | 6/2000 |
| WO | WO 01/15614 | 3/2001 |
| WO | WO 01/54604 | 8/2001 |
| WO | WO 02 071926 A2 | 9/2002 |
| WO | WO 2005/110264 | 11/2005 |

(56) References Cited

FOREIGN PATENT DOCUMENTS

| WO | 2007/019268 A2 | 2/2007 |
|---|---|---|
| WO | 2010/118312 A2 | 10/2010 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
U.S. Appl. No. 12/692,414, filed Jan. 22, 2010, Peter M. Mueller.
U.S. Appl. No. 12/696,592, filed Jan. 29, 2010, Jennifer S. Harper.
U.S. Appl. No. 12/696,857, filed Jan. 29, 2010, Edward M. Chojin.
U.S. Appl. No. 12/700,856, filed Feb. 5, 2010, James E. Krapohl.
U.S. Appl. No. 12/719,407, filed Mar. 8, 2010, Arlen J. Reschke.
U.S. Appl. No. 12/728,994, filed Mar. 22, 2010, Edward M. Chojin.
U.S. Appl. No. 12/748,028, filed Mar. 26, 2010 Jessica E.C. Olson.
U.S. Appl. No. 12/757,340, filed Apr. 9, 2010, Carine Hoarau.
U.S. Appl. No. 12/758,524, filed Apr. 12, 2010, Duane E. Kerr.
U.S. Appl. No. 12/759,551, filed Apr. 13, 2010, Glenn A. Horner.
U.S. Appl. No. 12/769,444, filed Apr. 28, 2010, Glenn A. Horner.
U.S. Appl. No. 12/770,369, filed Apr. 29, 2010, Glenn A. Horner.
U.S. Appl. No. 12/770,380, filed Apr. 29, 2010, Glenn A. Horner.
U.S. Appl. No. 12/770,387, filed Apr. 29, 2010, Glenn A. Horner.
U.S. Appl. No. 12/773,526, filed May 4, 2010, Duane E. Kerr.
U.S. Appl. No. 12/773,644, filed May 4, 2010, Thomas J. Gerhardt.
U.S. Appl. No. 12/786,589, filed May 25, 2010, Duane E. Kerr.
U.S. Appl. No. 12/791,112, filed Jun. 1, 2010, David M. Garrison.
U.S. Appl. No. 12/792,001, filed Jun. 2, 2010, Duane E. Kerr.
U.S. Appl. No. 12/792,008, filed Jun. 2, 2010, Duane E. Kerr.
U.S. Appl. No. 12/792,019, filed Jun. 2, 2010, Duane E. Kerr.
U.S. Appl. No. 12/792,038, filed Jun. 2, 2010, Glenn A. Horner.
U.S. Appl. No. 12/792,051, filed Jun. 2, 2010, David M. Garrison.
U.S. Appl. No. 12/792,068, filed Jun. 2, 2010, Glenn A. Horner.
U.S. Appl. No. 12/792,097, filed Jun. 2, 2010, Duane E. Kerr.
U.S. Appl. No. 12/792,262, filed Jun. 2, 2010, Jeffrey M. Roy.
U.S. Appl. No. 12/792,299, filed Jun. 2, 2010, Jeffrey M. Roy.
U.S. Appl. No. 12/792,330, filed Jun. 2, 2010, David M. Garrison.
U.S. Appl. No. 12/822,024, filed Jun. 23, 2010, Peter M. Mueller.
U.S. Appl. No. 12/821,253, filed Jun. 23, 2010, Edward M. Chojin.
U.S. Appl. No. 12/832,772, filed Jul. 8, 2010, Gary M. Couture.
U.S. Appl. No. 12/843,384, filed Jul. 26, 2010, David M. Garrison.
U.S. Appl. No. 12/845,203, filed Jul. 28, 2010, Gary M. Couture.
U.S. Appl. No. 12/853,896, filed Aug. 10, 2010, William H. Nau, Jr.
U.S. Appl. No. 12/859,896, filed Aug. 20, 2010, Peter M. Mueller.
U.S. Appl. No. 12/861,198, filed Aug. 23, 2010, James A. Gilbert.
U.S. Appl. No. 12/861,209, filed Aug. 23, 2010, William H. Nau, Jr.
U.S. Appl. No. 12/876,668, filed Sep. 7, 2010, Sara E. Anderson.
U.S. Appl. No. 12/876,680, filed Sep. 7, 2010, Peter M. Mueller.
U.S. Appl. No. 12/876,705, filed Sep. 7, 2010, Kristin D. Johnson.
U.S. Appl. No. 12/876,731, filed Sep. 7, 2010, Kristin D. Johnson.
U.S. Appl. No. 12/877,199, filed Sep. 8, 2010, Arlen J. Reschke.
U.S. Appl. No. 12/877,482, filed Sep. 8, 2010, Gary M. Couture.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/029,390, filed Feb. 17, 2011, Michael C. Moses.
U.S. Appl. No. 13/030,231, filed Feb. 18, 2011, Jeffrey M. Roy.
U.S. Appl. No. 13/050,182, filed Mar. 17, 2011, Glenn A. Horner.
U.S. Appl. No. 13/072,945, filed Mar. 28, 2011, Patrick L. Dumbauld.
U.S. Appl. No. 13/075,847, filed Mar. 30, 2011, Gary M. Couture.
U.S. Appl. No. 13/080,383, filed Apr. 5, 2011, David M. Garrison.
U.S. Appl. No. 13/083,962, filed Apr. 11, 2011, Michael C. Moses.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, Vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.

(56) References Cited

OTHER PUBLICATIONS

Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/ Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234, No. 1, Jul. 2001; pp. 21-24.
Levy et al., "Update on Hysterectomy—New Technologies and Techniques"OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.

(56) References Cited

OTHER PUBLICATIONS

Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 185386.9 dated Jan. 10, 2011.
Int'l Search Report EP 10 185405.7 dated Jan. 5, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182022.3 dated Mar. 11, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 161117.4 dated Jun. 30, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/USO4/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
International Search Report from International Application No. PCTUS2012/045762 mailed Feb. 26, 2013(12 pgs.).
European Search Report dated Feb. 10, 2015 for corresponding EP applcation No. EP 12 81 1491, 7 pages.

* cited by examiner

STAND ALONE ENERGY-BASED TISSUE CLIPS

BACKGROUND

1. Technical Field

The present disclosure relates to the use of energy-based electrosurgical instruments. More particularly, the present disclosure is directed to the use of stand alone energy-based tissue clips to provide energy to seal, cauterize, ablate or destroy cells and/or tissue.

2. Background of the Related Art

Surgical staplers are widely used to join or bond tissues together and to provide hemostasis of adjacent tissues. These staples can be employed in combination with electrosurgical stapling apparatus where thermogenic energy is utilized to provide short-term hemostasis and sealing. One drawback of using staples is that staples generally remain inside the body.

Another method of joining or bonding tissue is based on radio frequency (RF) energy applied to tissue. Existing RF energy-based tissue sealing instruments utilize metal electrodes combined with jaws which grasp and hold sealed tissue. Energy-based tissue sealing involves compressing tissue to bring vessel walls together, heating compressed tissue by RF current up to the temperature of denaturizing and mixing of collagen and elastin, and cooling down and solidification of the melted collagen and elastin to form the seal.

This approach has several disadvantages which are inherent to most energy-based sealing instruments. Compressing and heating of tissue takes considerable time in which the surgeon has to hold the instrument and wait. This may interfere with the continuous flow of a surgical procedure. In order to reduce sealing time, power has to be increased that may result in higher risk of thermal damage and to more bulky instrument and generator designs. Additionally, after several cycles of successive sealing, the jaw members of the electrosurgical instrument may become overheated and a surgeon may need to wait until they cool to avoid poor quality sealing and thermal damage of adjacent tissues.

SUMMARY

In an embodiment of the present disclosure, a tissue clip is provided having an arm with a first electrode and a body pivotally coupled to the arm. The body includes a power source and a second electrode. The arm is moveable from a first position relative to the body for approximating tissue and a second position closer to the body for grasping tissue therebetween.

The body may include an antenna configured to transfer energy from the power source to the first and/or second electrode. The body may also include an antenna configured to communicate with an external control unit. The tissue clip may further include a sensor array to determine tissue parameters of tissue between the arm and the body.

In one embodiment, the first electrode and/or second electrode may include a stainless steel layer and a copper layer. Alternatively, the first and/or second electrode may include at least one piezo electric sensor. In another embodiment, the first electrode may include an outer layer composed of a non-stick material and flex circuit having a coil formed thereon.

The first electrode and second electrode cooperate with the control unit and the power source to seal tissue. The tissue clip may also include a cutting element having an electrode configured to electrically cut tissue. The cutting element cooperates with a control unit to cut tissue after seal is completed. The tissue clip may also include at least one sensor configured to sense a completed seal and the control unit automatically activates the cutting element when the at least one sensor senses the completed seal.

In yet another embodiment, the first electrode includes a first pair of tissue contacting surfaces and an insulator disposed therebetween and the second electrode includes a second pair of tissue contacting surfaces and a pair of insulators disposed between the second pair of tissue contacting surfaces. A cutting element is disposed between the pair of insulators. The cutting element may be moveable to cut tissue before, during or after the formation of a tissue seal. The cutting element includes an electrode that is configured to electrically cut tissue In another embodiment of the present disclosure, a tissue clip is provided that includes an arm having a fiber grating and a body pivotally coupled to the arm. The body includes a power source, a fiber grating and a light source coupled to the fiber grating in the arm and the fiber grating in the body. The arm is moveable from a first position relative to the body for approximating tissue and a second position closer to the body for grasping tissue therebetween.

The body may include a control unit configured to transfer energy from the power source to the light source to.

The fiber grating in the arm and the fiber grating in the body cooperate with the control unit and the power source to seal tissue.

The arm and/or the body includes a cutting mechanism configured to cut tissue disposed between the arm and the body wherein the cutting mechanism cuts the tissue disposed between the arm and the body before, during or after the tissue is sealed. The cutting mechanism may include an electrode configured to electrically cut tissue. The cutting mechanism cooperates with a control unit to cut tissue after seal is completed. Alternatively, the cutting mechanism may include a light source configured to emit a focused light to cut tissue.

In yet another embodiment of the present disclosure, a tissue clip is provided that includes an electrode assembly, a first arm, a second arm moveable from a first position relative to the first arm to approximate tissue to a second position closer to the first arm for grasping tissue therebetween, a first electrode disposed on the first arm, a second electrode disposed on the second arm, and The electrode assembly is configured to seal tissue and may cooperate with a control unit to seal tissue. The electrode assembly may also include a pair of first terminals coupled to the first electrode and the second electrode.

The tissue clip may also include a body having a power source, a control unit coupled to the power source and a pair of second terminals coupled to control unit, the pair of second terminals configured to receive the pair of first terminals. The electrode assembly may be removably coupled to the body.

The electrode assembly may be absorbable and the body may be reusable. In one embodiment, the power source may be removably coupled to the body. In another embodiment, the power source is included in the body. The power source may also be removably coupled to the electrode assembly.

In yet another embodiment of the present disclosure, a tissue clip is provided having an electrode assembly with a first electrode and a retaining clip. The tissue clip also includes a body having a second electrode and a power source. The retaining clip couples the electrode assembly to the body to grasp tissue between the first electrode and the second electrode.

The body may include a control unit coupled to the power source. The electrode assembly may further include a power source, and at least one sensor to determine a parameter of the tissue grasped between the first electrode and the second electrode. The electrode assembly may also include a control unit coupled to the power source wherein the control unit controls sealing of tissue.

The body further includes at least one sensor to determine a parameter of the tissue grasped between the first electrode and the second electrode. The power source in the body may provide energy to the first electrode.

In yet another embodiment of the present disclosure, a method for sealing tissue is provided. The method includes providing a tissue clip having a first portion having a first electrode and a second portion removably coupled to the first portion. The second portion includes a power source, a second electrode and a control unit configured to transfer energy from the power source to the first and/or second electrode. After providing the tissue clip, tissue is approximated between the first portion and the second portion. The tissue is grasped between the first portion and the second portion by moving the first portion from a first position relative to the second portion for approximating tissue to a second position closer to the second portion for grasping tissue therebetween. Then the power source is activated to seal tissue.

In yet another embodiment of the present disclosure, a tissue sealing system may be provided that includes an external control unit and a tissue clip. The external control unit includes a power source and a transmitting coil. The tissue clip includes a body, a first arm movable relative to the body to grasp tissue and a receiving coil operatively coupled to at least one electrode disposed in one of the body and/or first arm. The transmitting coil induces a current in the receiving coil that is supplied to the at least one electrode to thermally treat tissue.

In yet another embodiment, a tissue clip is provided that includes a control portion having a power source and a clip portion. The clip portion includes a first arm, a second arm, and at least one electrode. The clip portion may be removably coupled from the control portion. The control portion may also include a control unit configured to transfer energy from the power source to the at least one electrode.

In one embodiment, the clip portion includes a shape memory alloy, wherein the first arm moves relatively closer to the second arm when the tissue clip is heated. In another embodiment, the clip portion includes a spring member configured to bias the first arm toward the second arm. The first arm and the second arm apply a closure pressure to seal tissue between 3 kg/cm$^2$ to 16 kg/cm$^2$.

In yet another embodiment, a tissue clip is provided having a first arm, a second arm, and helical torsion spring. The first arm includes a power source and at least one electrode. The helical torsion spring is configured to couple the first arm to the second arm. The helical coil spring biases a proximal end of the first arm toward the proximal end of the second arm to grasp tissue therebetween. The helical torsion spring causes the first arm and the second arm to apply a closure pressure to seal tissue between 3 kg/cm$^2$ to 16 kg/cm$^2$. The tissue clip may also include at least one stop member configured to provide a gap between the first arm and the second arm during sealing in the range of 0.001 inches to 0.006 inches. The first arm may also include control unit configured to transfer energy from the power source to the at least one electrode.

In the embodiments described above, during a sealing procedure, the arms close with an appropriate closure pressure to seal tissue, e.g., 3 kg/cm$^2$ to 16 kg/cm$^2$.

As mentioned above, it is contemplated that the tissue clip embodiments described herein can use light, microwave, RF, or resistive energy to thermally treat tissue or seal tissue (as defined herein).

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1A:
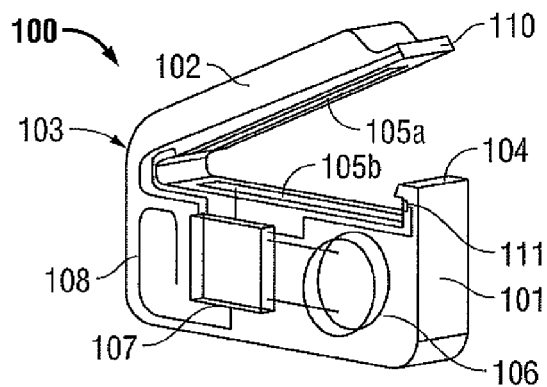
FIG. 1A is a schematic diagram of a tissue clip according to an embodiment of the present disclosure.

Particular embodiments of the present disclosure are described hereinbelow with reference to the accompanying drawings; however, the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Like reference numerals may refer to similar or identical elements throughout the description of the figures. As shown in the drawings and described throughout the following description, as is traditional when referring to relative positioning on a surgical instrument, the term "proximal" refers to the end of the apparatus that is closer to the user and the term "distal" refers to the end of the apparatus that is farther away from the user. The term "clinician" refers to any medical professional (e.g., doctor, surgeon, nurse, or the like) performing a medical procedure involving the use of embodiments described herein.

Electromagnetic energy is generally classified by increasing frequency or decreasing wavelength into radio waves, microwaves, infrared, visible light, ultraviolet, X-rays and gamma-rays. As used herein, the term "microwave" generally refers to electromagnetic waves in the frequency range of 300 megahertz (MHz) ($3\times10^8$ cycles/second) to 300 gigahertz (GHz) ($3\times10^{11}$ cycles/second). As used herein, the term "RF" generally refers to electromagnetic waves having a lower frequency than microwaves. As used herein, the term "ultrasound" generally refers to cyclic sound pressure with a frequency greater than the upper limit of human hearing. The terms "tissue" and "vessel" may be used interchangeably since it is believed that the present disclosure may be employed to seal and cut tissue or seal and cut vessels utilizing the same principles described herein.

The present disclosure is directed to the use of tissue clips in electrosurgical procedures. The tissue clips can be installed and configured to operate independently. When a clip is used on a vessel, the clip can stop blood flow immediately after installation and lets a surgeon proceed without waiting until the installed clip completes the vessel sealing procedure.

The use of the tissue clips in a vessel sealing procedure involves providing a tissue clip that may be any one of the tissue clips described hereinbelow. The tissue clip is placed in the body of a patient approximately near tissue that will be sealed and/or cut. The tissue is then grasped by the tissue clip using one of the mechanisms described below. Energy is provided to the tissue from the power source and the grasped tissue is then sealed before the tissue clip is removed.

As will be described in more detail below, the clip can be positioned on a vessel and then set into the closed position using a suitable surgical instrument such as forceps. The closed position provides vessel deformation and stops the blood flow. After a clip is installed and detached from the forceps or like instrument, energy is applied to the grasped tissue and the sealing process begins.

When using the tissue clips of the present disclosure, sealing time is not as crucial as for typical energy-based instruments. Longer sealing time lowers the requirements for a power source and, as such, enables more compact designs and reduces risk of thermal damage. The use of such tissue clips also enables the use of different sealing mechanisms such as soldering and photochemical tissue bonding which require a longer time then RF based sealing.

Referring to FIG. 1A, a tissue clip according to an embodiment of the present disclosure is shown generally as tissue clip 100. Tissue clip 100 may be used for monopolar or bipolar electrosurgical procedures. Tissue clip 100 includes a body 101 and arm 102. Arm 102 is connected to body 101 via a flexible joint 103. A hinge or other pivoting mechanism may be used instead of flexible joint 103. Flexible joint 103 allows the other end of arm 102 to move with respect to body 101. Body 101 includes a protrusion or latch 104 which fixes or selectively locks arm 102 in the closed position. Tissue that is to be sealed is placed between body 101 and arm 102. A gap may be provided by the flexible hinge 103 or stop members 190 (FIG. 6) may be used to determine the gap between body 101 and arm 102 to provide optimal tissue thickness for a particular sealing mechanism. Typically, the gap is in the range of 0.001 inches to about 0.006 inches Tissue clip 100 includes electrodes 105a and 105b on arm 102 and body 101, respectively. A power source 106 and control unit 107 are provided in body 101 to provide the necessary voltage to electrodes 105a and 105b. Control unit 107 transfers electrical power from power source 106 to electrodes 105a and 105b and applies a 100 KHz to 10 MHz frequency to electrodes 105a and 105b. The voltage profile provided by control unit 107 may be predetermined and stored in control unit 107 or provided by an external control unit 202 (FIG. 2) via antenna 108. Alternatively, the voltage profile may be adjusted by sensor array 170 (FIG. 6) that determines one or more parameters of the grasped tissue measured before or during a sealing process.

Figure 1B:
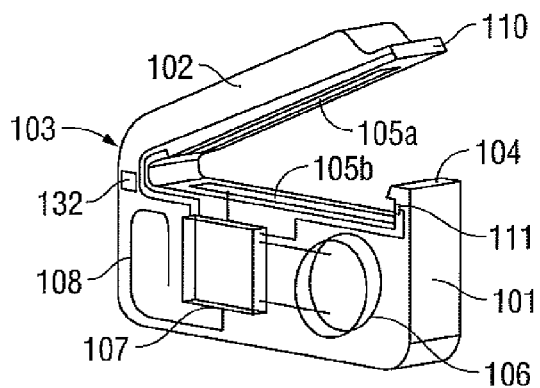
FIG. 1B is a schematic diagram of a tissue clip according to another embodiment of the present disclosure.
Figure 1C:
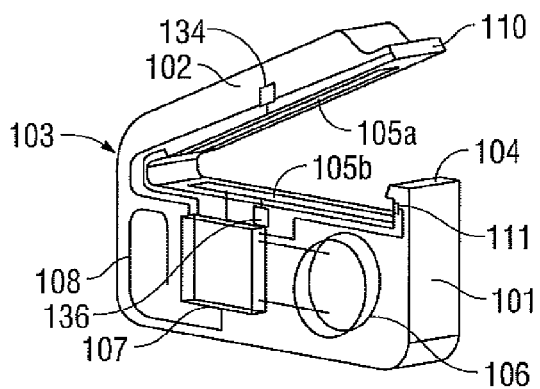
FIG. 1C is a schematic diagram of a tissue clip according to another embodiment of the present disclosure.

In addition to the energy being applied to tissue grasped between body 101 and arm 102, body 101 and arm 102 applies a sealing pressure to tissue grasped therebetween. In one embodiment, the sealing pressure is in the range of 3 Kg/cm² to 16 Kg/cm². Sealing pressure may be applied using different methods as shown in FIGS. 1A-1C. For instance, as shown in FIG. 1A, when arm 102 is locked in the closed position by protrusion 104, a predetermined sealing pressure is maintained. Alternatively, a biasing member may be provided to generate the appropriate sealing pressure. A biasing member 132 may be substituted for hinge 103, as shown in FIG. 1B or a biasing member 134, 136 may be attached to electrodes 105a and 105b, as shown in FIG. 1C.

In FIG. 1B, biasing member 132 is used to move arm 102 from a first position to a second position closer to body 101 to grasp tissue. Biasing member 132 may be a spring loaded component that applies a predetermined sealing pressure to grasped tissue. Alternatively, biasing member 132 may be driven by a motor that may be manufactured using microelectromechanical systems (MEMS) technology. The motor may be controlled by control unit 107 based on: a sealing pressure detected by sensor array 170 (FIG. 6); an algorithm stored in control unit 107; an algorithm provided to control unit 107 from control unit 202; or a user input provided from control unit 202.

In FIG. 1C, biasing members 134 and 136 may be attached to electrodes 105a and 105b, respectively. Although two biasing members are shown, a single biasing member attached to one electrode or both electrodes may be used. Biasing members 134 and 136 may be a spring-loaded component that moves at least one of the electrodes toward or away from each other to apply a predetermined sealing pressure to grasped tissue. Alternatively, biasing members 134 and 136 may be driven by a motor that may be manufactured using MEMS technology. The motor may be controlled by control unit 107 based on: a sealing pressure detected by sensor array 170 (FIG. 6); an algorithm stored in control unit 107; an algorithm provided to control unit 107 from control unit 202; or a user input provided from control unit 202.

Figure 2:
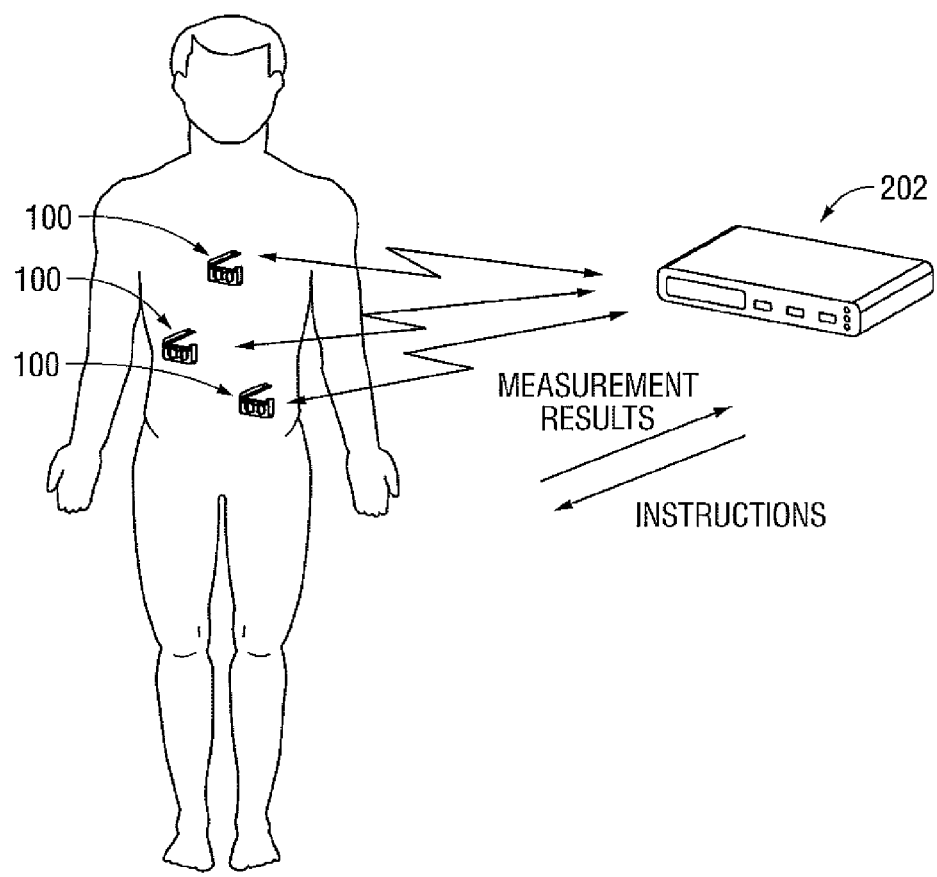
FIG. 2 is a schematic diagram of an electrosurgical system utilizing tissue clips according to an embodiment of the present disclosure.
Figure 3:
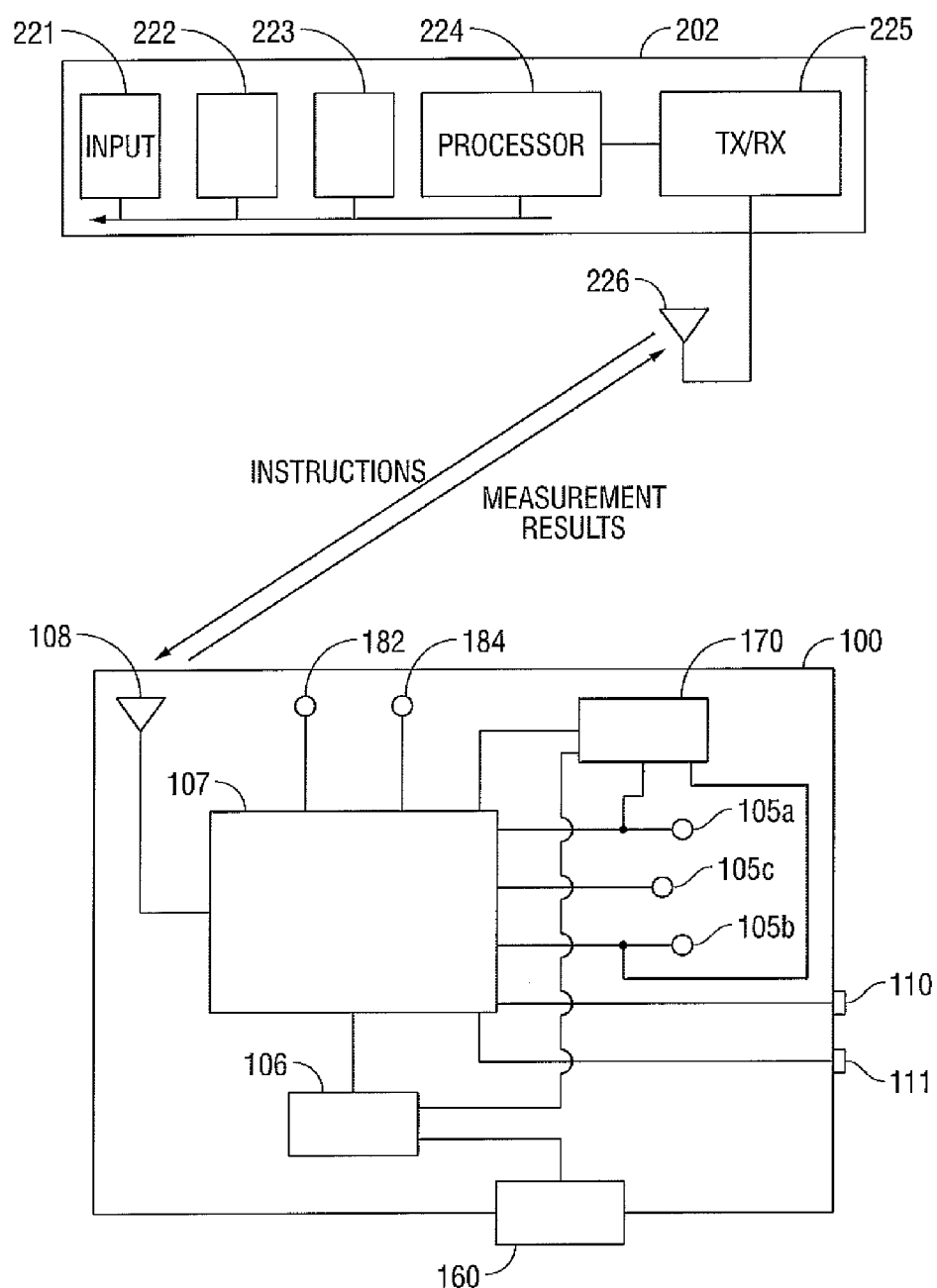
FIG. 3 is a system block diagram according to an embodiment of the present disclosure.

The tissue clips may be used with an external control unit 202, as shown in FIGS. 2 and 3. Control unit 202 may communicate with tissue clips 100 using suitable methods such as Bluetooth communication, radio communication, communication similar to the use of radio frequency identification tags or any other wireless communication. External control unit may transmit instructions to tissue clips 100 while tissue clips 100 may transmit results as well as measured tissue parameters. Based on the received data, control unit 202 may send instructions to tissue clips 100, which set the voltage and frequency according to the received instructions. One external control unit 202 may be used to control multiple tissue clips.

FIG. 3 depicts a system block diagram of an embodiment of the present disclosure. Control unit 202 may include an input device 221, a display 222, memory 223, processor 224 and a transceiver 225 coupled to an antenna 226. Input device 221 may include buttons, knobs, switches or the like to input information for control unit 202 as well as tissue clips 100. Display 222 may show the status of the vessel sealing procedure, parameters measured by sensor array 170, status of individual tissue clips (e.g., malfunction, damaged, properly working, battery life, etc.) and time left in the electrosurgical procedure, time elapsed during the electrosurgical procedure.

Memory 223 may be volatile type memory (e.g., RAM) and/or non-volatile type memory (e.g., flash media, disk media, etc.) that stores programs or sets of instructions that may be used to control the vessel sealing procedure. Processor 224 may be an integrated circuit or may include analog and/or logic circuitry that may be used to: execute instructions according to inputs provided by the input device 221 or sensor array 170, execute instructions according to a program provided in memory 223; and control operation of control unit 202 and/or tissue clip 100. The processor 224 sends a control signal to tissue clip 100 via transceiver 225 and antenna 226.

Control unit 202 transmits instructions to tissue clip 100, which receives the instructions through antenna 108. The instructions are decoded by control unit 107, which then transfers power from power source 106 to electrodes 105a and 105b according to the received instructions. Control unit 107 may apply energy to a terminal 105c that may be coupled to an electrode 1026 (FIG. 10) to be used for cutting tissue.

Control unit 107 may perform a diagnostic check on tissue clip 100. If the tissue clip is defective or malfunctioning, a red light emitting diode (LED) 182 may be illuminated. If the tissue clip is functioning properly, a green LED 184 may be lit. Tissue clip also includes a sensor array 170 that determines properties of tissue between electrodes 105a and 105b as well as output voltage, current, impedance and power from control unit 107. The detected tissue properties provide feedback to the control unit 107 or external control unit 202 to control the output of control unit 107 via an open loop or closed loop scheme.

Power source 106 may be a rechargeable battery and may be coupled to a terminal 160 that may be used to recharge power source 106. As shown on FIG. 1A, arm 102 may have a contact 110 and body 101 may have a contact 111 as a safety check. The tissue clip is not operational until contact 110 is electrically coupled to contact 111.

Figure 4:
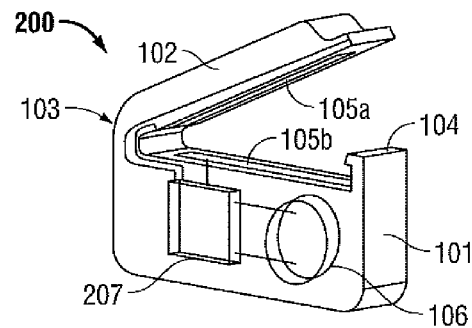
FIG. 4 is a schematic diagram of a tissue clip according to another embodiment of the present disclosure.
Figure 5:
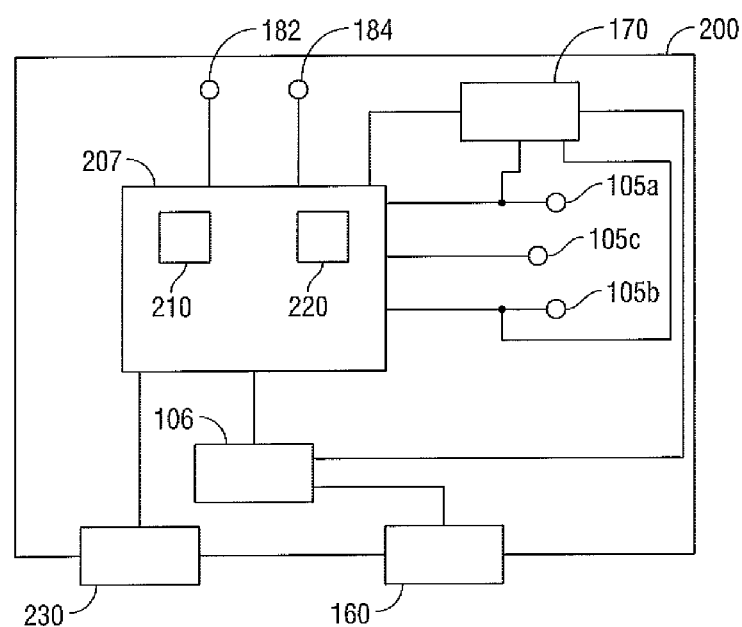
FIG. 5 is a system block diagram of the tissue clip of FIG. 4.

FIGS. 4 and 5 depict a tissue clip according to another embodiment of the present disclosure shown generally as 200. As shown in FIGS. 4 and 5, tissue clip 200 includes a control unit 207. Control unit 207 includes a memory 210 and a processor 220. Memory 210 may include a program or set of instructions that can be used to control the voltage output of control unit 207. Tissue clip 200 may also include a terminal 230 that may be used to store instructions in memory 207, determine the status of the tissue clip, record tissue parameters detected by sensor array 170 of tissue clip 200. Tissue clip 200 may also include any of the biasing members described above with regard to FIGS. 1B and 1C.

Figure 6:
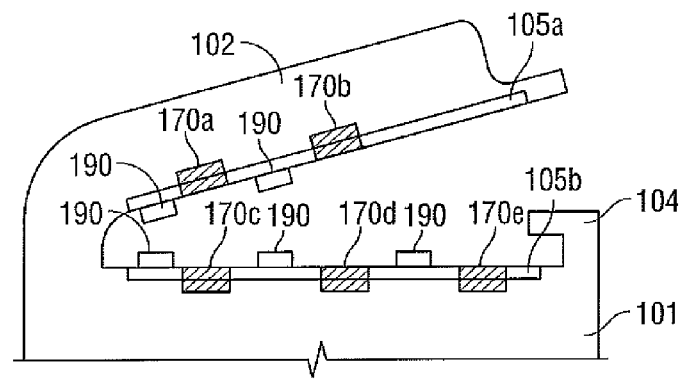
FIG. 6 is a schematic diagram of a jaw portion according to an embodiment of the present disclosure.

As shown in FIG. 6, an array of sensors 170a-170e are positioned within a cavity defined between arm 102 and body 101. The sensors 170a-170e are configured to automatically sense various properties of the tissue disposed between the arm 102 and body 101 and provide feedback to the control unit 107, 207 or 202 during the sealing process. Such properties include, but are not limited to: tissue impedance, tissue type, tissue clarity, tissue compliance, temperature of the tissue or jaw members, water content in tissue, jaw opening angle, water motility in tissue, energy delivery sealing pressure and/or jaw closure pressure. During the sealing process, the sensors 170a-170e, control unit 107, 207, and/or 202, all cooperate to regulate the sealing procedure on tissue to conform to a predetermined algorithm.

As mentioned above, the arm 102 and/or body 101 may include one or more stop members 190 which limit the movement of the arm 102 and/or body 101 relative to one another. The stop member(s) 190 may be configured to extend from the electrode 105a and/or 105b a predetermined distance according to the specific material properties (e.g., compressive strength, thermal expansion, etc.) to yield a consistent and accurate gap distance "G" during sealing. In some embodiments, the gap distance between the arm 102 and body 101 during sealing ranges from about 0.001 inches to about 0.006 inches and, in one particularly useful embodiment, between about 0.002 and about 0.003 inches. The non-conductive stop member(s) 190 may be molded onto the arm 102 and/or body 101 (e.g., overmolding, injection molding, etc.), stamped onto the arm 102 and/or body 101 or deposited (e.g., deposition) onto the arm 102 and/or body 101.

Figure 7:
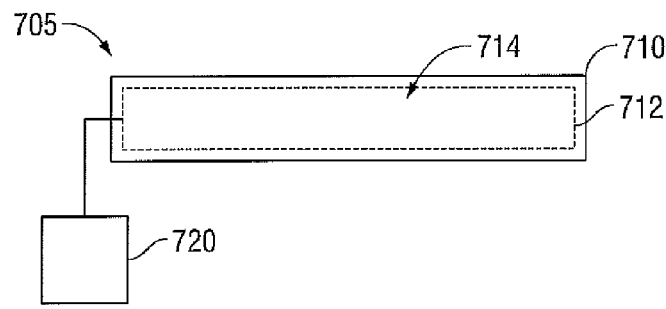
FIG. 7 is a schematic block diagram of an electrode suitable for use in a tissue clip according to another embodiment of the present disclosure.

Turning to FIG. 7, an electrode suitable for use in a tissue clip according to another embodiment of the present disclosure is shown generally as 705. As shown in FIG. 7, electrode 705 includes a stainless steel layer 710 and a copper layer 712. Copper layer 712 partially covers stainless steel layer 710. Electrode 705 may be formed by cladding a sheet of copper to a sheet of stainless steel and then stamping out or machining the bonded sheets into the shape of electrode 705. Then a photolithography procedure may be used to etch portions of the copper from the edges of the electrode 705 leaving a heating section 714. By etching out the copper from electrode 705, only heating section 714 applies heat to tissue during a vessel sealing procedure. By not applying heat along the edges of electrode 705, charring of tissue during a vessel sealing procedure may be reduced. An energy source 720, which may include a control unit and/or battery as described above, may be used to provide electrosurgical energy to electrode 705.

Figure 8:
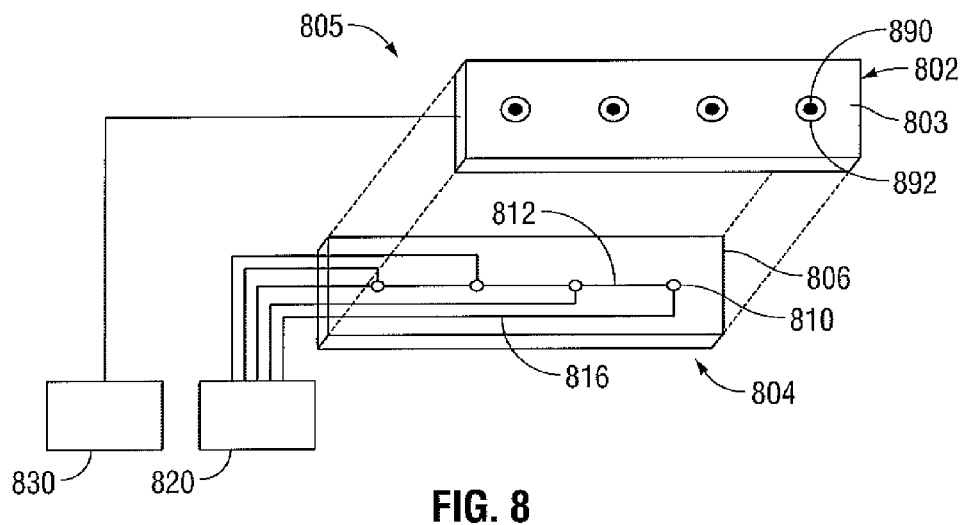
FIG. 8 is a schematic block diagram of an electrode suitable for use in a tissue clip according to another embodiment of the present disclosure.

Turning to FIG. 8, an exploded view of electrode 805 suitable for use in a tissue clip according to another embodiment of the present disclosure is shown. Electrode 805 includes an insulative plate 804 that is a flex circuit. Flex circuits are used to assemble electronic circuits by mounting electronic devices on flexible plastic substrates. Such plastic substrates may include, but are not limited to, polyimide or polyether ether ketone (PEEK) film. Flex circuits may also be constructed by screen printing silver circuits onto polyester. As shown in FIG. 8 insulative plate 804 has a substrate 806 having circuit traces 812 formed thereon. Circuit traces 812 may be made from copper, silver, or any other electrical conductor. Circuit traces 812 may be formed by any suitable method. For instance, circuit traces 812 may be formed by adhering a conductive layer to substrate 806. Using photolithography, a mask outlining circuit traces 812 may be formed and then the conductive layer may be etched to leave circuit traces 812.

Circuit traces 812 include contacts 810 that may be made from copper, silver or any other electrical conductor. Contacts 810 may be made from the same material as circuit traces 812 or from a material different from circuit traces 812. Each contact 810 is operatively coupled to sensor array 820 via contact traces 816. Contacts 810 and contact traces 816 are formed using the same techniques that may be used to form circuit traces 812. The location of contacts 810 correspond to the location of piezo electric sensors 890. Accordingly, when piezo electric sensors 890 measure or detect a tissue property, piezo electric sensors 890 provide a signal to controller 820 indicative of tissue properties via contacts 810 and contact traces 816.

Electrode 805 includes a seal plate 802. Seal plate 802 is made from stainless steel, and as described above, has piezo electric sensors 890 disposed therein in locations 892. Seal plate 802 may be formed by any suitable method. For instance, a layer of stainless steel may be provided and shaped to form seal plate 802. Then, a photolithography mask is applied to seal plate 802 leaving locations 892 exposed. An etching solution is applied to seal plate 802 to etch away exposed locations 892. Then the mask is removed leaving seal plate 802 with locations 892 etched away. When electrode 805 is assembled, piezo electric sensors 890 are placed in locations 892 of seal plate 802 and are coupled to contacts 810 of insulative plate 804.

Figure 9:
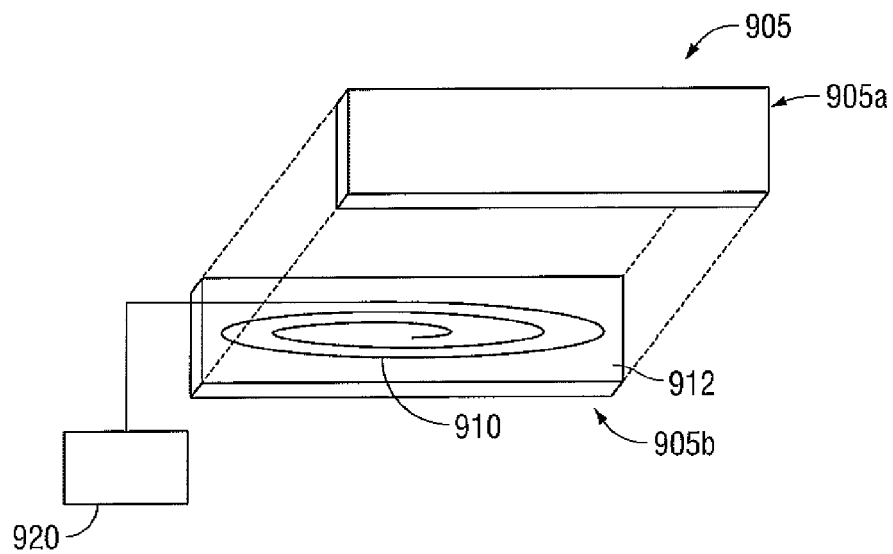
FIG. 9 is a schematic block diagram of an electrode suitable for use in a tissue clip according to another embodiment of the present disclosure.

Turning to FIG. 9, an electrode suitable for use in a tissue clip according to another embodiment of the present disclosure generally designated as 905 is shown. Electrode 905 is located on an arm of a tissue clip (e.g., 102 of tissue clip 100) and has an outer layer 905a formed from glass or other isolative non-stick material. Layer 905b may be a flex circuit having a coil 910 formed on a flexible plastic substrate 912. Such flexible plastic substrates 912 may be formed from, but are not limited to, polyimide, polyether ether ketone (PEEK) film or polylaminate. Flex circuits may also be constructed by screen printing silver circuits onto polyester.

Coil 910 may be made from copper, silver, or any other electrical conductor. Coil 910 may be formed by any suitable method. For instance, coil 910 may be formed by adhering a conductive layer to flexible plastic substrate 912. Using photolithography, a mask outlining coil 910 may be formed and then the conductive layer may be etched to leave coil 910. Coil 910 may be coupled to an energy source 920.

When energy is applied to coil 910 in electrode 905 and a steel plate (not shown) located on a body of a tissue clip (e.g., body 101 of tissue clip 100) is positioned within an electromagnetic field caused by the application of energy to coil 910, heat is generated in tissue disposed between electrode 905 and the steel plate. Electrode 905 may have one or more coatings of a non-stick material. Therefore, tissue would not touch hot metal surfaces and sticking would be reduced. Further, since no heat energy would be applied to the electrode 905 (heat is generated in the tissue) the efficiency and speed of the seal would increase.

Figure 10:
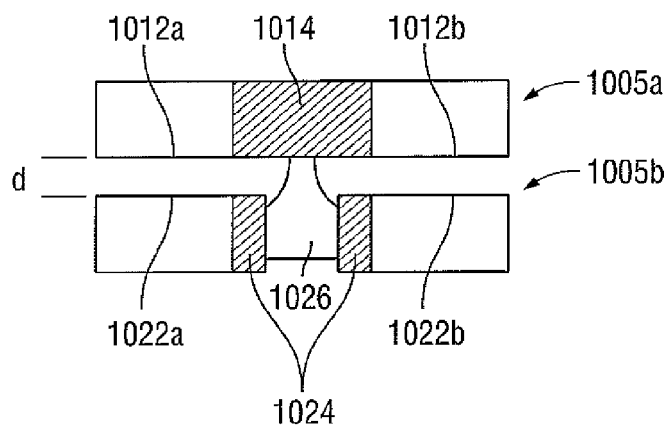
FIG. 10 is a cross sectional view of an electrode assembly of a tissue clip according to another embodiment of the present disclosure.

As seen in FIG. 10, an electrode assembly 1005 having a first electrode 1005a located on an arm of the tissue clip (e.g., arm 102 of FIG. 1A) and a second electrode 1005b on a body of the tissue clip (e.g., body 101 of FIG. 1A) are shown and are designed to effectively seal and cut tissue disposed between sealing surfaces 1012a, 1012b and 1022a, 1022b and cutting element 1026 of the opposing electrodes 1005a and 1005b, respectively. More particularly, and with respect to FIG. 10, electrodes 1005a and 1005b include conductive tissue contacting surfaces 1012a, 1012b and 1022a, 1022b, respectively, disposed along substantially the entire longitudinal length thereof (e.g., extending substantially from the proximal to distal end of the respective arm and body of a tissue clip). Tissue contacting surfaces 1012a, 1012b and 1022a, 1022b may be attached to arm or body by stamping, by overmolding, by casting, by overmolding a casting, by coating a casting, by overmolding a stamped electrically conductive sealing plate and/or by overmolding a metal injection molded seal plate or in other suitable ways.

With respect to FIG. 10, the opposing electrodes 1005a and 1005b both include an insulator or insulative material 1014 and 1024, respectively, disposed between each pair of electrically conductive sealing surfaces on the opposing electrodes 1005a and 1005b, e.g., between pairs 1012a and 1012b and between pairs 1022a and 1022b. Insulator 1014 is generally centered between tissue contacting surfaces 1012a, 1012b thereof along substantially the entire length the arm of the tissue clip. Insulators 1024 are generally centered along substantially the entire length of the body of the tissue clip. Insulators 1014 and 1024 are arranged such that the insulator 1014 generally opposes insulators 1024.

One or all of the insulators 1014 and 1024 may be made from a ceramic material due to the hardness of the ceramic and inherent ability to withstand high temperature fluctuations. Alternatively, one or both of the insulators 1014 and 1024 may be made from a material having a high Comparative Tracking Index (CTI) having a value in the range of about 300 to about 600 volts. Examples of high CTI materials include nylons and syndiotaetic polystyrenes. Other suitable materials may also be utilized either alone or in combination, e.g., Nylons, Syndiotactic-polystyrene (SPS), Polybutylene Terephthalate (PBT), Polycarbonate (PC), Acrylonitrile Butadiene Styrene (ABS), Polyphthalamide (PPA), Polymide, Polyethylene Terephthalate (PET), Polyamide-imide (PAI), Acrylic (PMMA), Polystyrene (PS and HIPS), Polyether Sulfone (PES), Aliphatic Polyketone, Acetal (POM) Copolymer, Polyurethane (PU and TPU), Nylon with Polyphenylene-oxide dispersion and Acrylonitrile Styrene Acrylate.

Electrode 1005b includes an electrically conductive cutting element 1026 disposed substantially within insulators 1024. As described in detail below, the cutting element 1026 may play a dual role during the sealing and cutting processes, namely: 1) to provide the necessary gap distance between conductive surfaces 1012a, 1012b and 1022a, 1022b during the sealing process; and 2) to electrically energize the tissue along the previously formed tissue seal to cut the tissue along the seal. With respect to FIG. 10, cutting element 1026 is electrically conductive; however, cutting element 1026 may be made from an insulative material with a conductive coating disposed thereon. The distance between cutting element 1026 and insulator 1014 may be disposed within the range of about 0.000 inches to about 0.040 inches to optimize the cutting effect.

During the so called "sealing phase", the opposing electrodes 1005a and 1005b are closed about tissue and the cutting element 1026 may form the requisite gap between the opposing sealing surfaces 1012a, 1022a and 1012b, 1022b. During activation of the sealing phase, the cutting element 1026 is not necessarily energized such that the majority of the current is concentrated between opposing sealing surfaces, 1012a and 1022a and 1012b and 1022b, to effectively seal the tissue. Stop members (not shown) may also be employed to regulate the gap distance between the sealing surfaces in lieu of or in combination with cutting element 1026.

Cutting element 1026 may be configured to extend beyond the tissue contacting surfaces 1012a, 1012b and 1022a, 1022b such that cutting element 1026 acts as a stop member that creates a distance "d" between opposing conductive sealing surfaces 1012a, 1022a and 1012b, 1022b, which as mentioned above promotes accurate, consistent and effective tissue sealing. Distance "d" is typically within the above-mentioned gap range. In one embodiment, the distance "d" has a minimum distance of about 0.005 inches for proper effect without stopping the current flow between the cutting element 1026 and tissue contacting surfaces 1012a, 1012b and 1022a, 1022b. As can be appreciated, cutting element 1026 also prevents the opposing tissue contacting surfaces 1012a, 1022a and 1012b, 1022b from touching, which eliminates the chances of the forceps 10, 100 shorting during the sealing process.

During sealing, energy is applied to the tissue through the opposing sealing plates 1012a, 1022a and 1012b, 1022b to effect two tissue seals on either side of the insulators 1014 and 1024. During the cutting phase, sealing electrodes 1012a, 1012b and 1022a, 1022b are energized to a first potential "−" and cutting element 1026 is energized to the second electrical potential "+". As a result thereof, during the cutting phase, energy is transferred between cutting element 1026 and sealing electrodes 1012a, 1012b and 1022a, 1022b thereby cutting tissue disposed between electrodes 1005a and 1005b.

In another embodiment, control unit 107 is configured to determine when tissue grasped by the tissue clip is sealed based on tissue properties detected by sensor array 170. When the control unit determines that the tissue has been sealed, control unit 107 automatically provides energy to terminal 105c, which is coupled to cutting element 1026, to cut the tissue grasped by the tissue clip.

Figure 11:
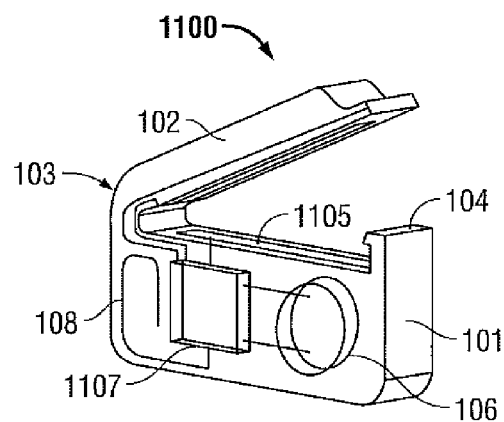
FIG. 11 is a schematic diagram of a tissue clip according to another embodiment of the present disclosure.
Figure 12:
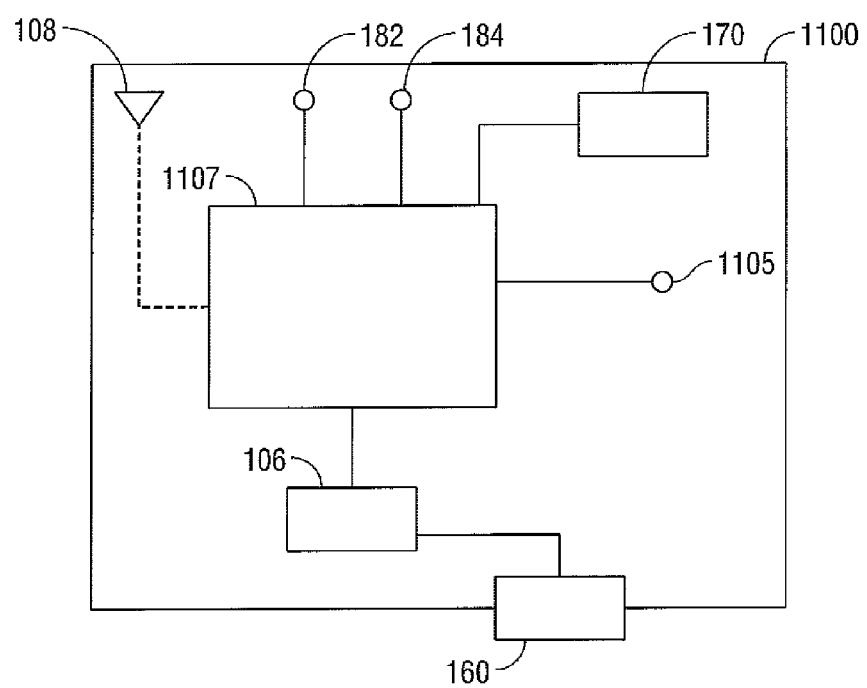
FIG. 12 is a system block diagram of the tissue clip of FIG. 11.

FIGS. 11 and 12 depict a tissue clip 1100 according to another embodiment of the present disclosure. As shown in FIGS. 11 and 12, tissue clip 1100 includes a control unit 1107 and a transducer 1105. Control unit 1107 transfers energy from power source 106 to transducer 1105 to apply ultrasonic energy to tissue disposed between arm 102 and body 101. As described above antenna 108 may receive instructions from an external control unit 202. Alternatively, control unit 1107 may include a memory and a processor. Memory may include a program or set of instructions that can be used to control the voltage output of control unit 1107. Tissue clip 1100 may also include any of the biasing members described above with regard to FIGS. 1B and 1C.

Figure 13A:
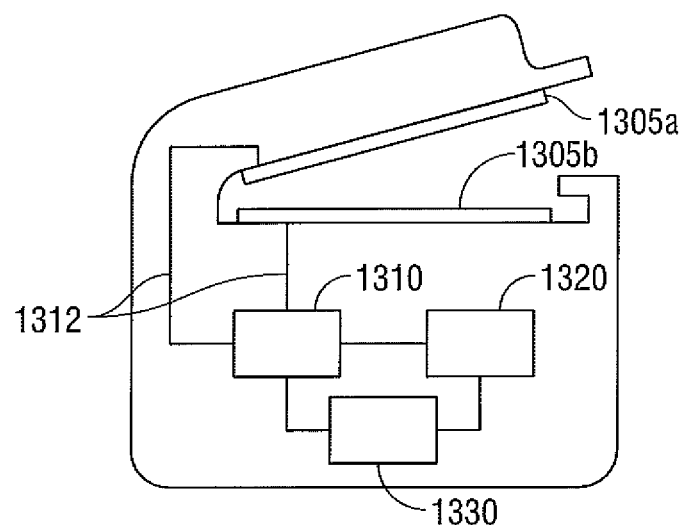
FIG. 13A is a schematic block diagram of a tissue clip according to another embodiment of the present disclosure.
Figure 13B:
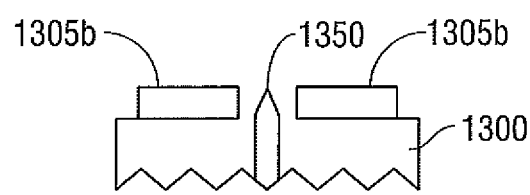
FIG. 13B is a schematic diagram of an electrode arrangement of the tissue clip of FIG. 13A.

FIGS. 13A and 13B depict a tissue clip according to another embodiment of the present disclosure shown generally as 1300. Tissue clip 1300 includes a power source 1330, control unit 1320 and a light source 1310. Light source 1310 may be coupled to long period fiber gratings 1305a and 1305b that emits light. Tissue clip 1300 may be used for optical soldering or photochemical tissue bonding. In the case of optical soldering, a soldering material may be applied (e.g., albumin) onto tissue between fiber gratings 1305a and 1305b. The soldering material may have a dye added thereto to reduce the amount of energy required due to the dye's absorption of certain wavelengths which is not absorbed by tissue. Light then heats the dye which in turn heats the solder. In the case of photochemical tissue bonding, a photosensitizer is added to the vessel before it is activated by light. This results in establishing covalent cross links without collagen denaturizing or heat-induced tissue damage. Tissue clip 1300 may also include any of the biasing members described above with regard to FIGS. 1B and 1C.

As shown in FIG. 13B, a cutting element 1350 is disposed between fiber grating 1305b. Cutting element 1350 is selectively moveable from a first position below the surface of fiber grating 1305b to a second position to cut tissue grasped by tissue clip 1300. Although FIG. 13b depicts the cutting mechanism disposed in the body between fiber grating 1305b, cutting mechanism 1350 patent may be disposed in the arm between fiber rating 1305a. Cutting mechanism 1350 may be incorporated into any of the embodiments described herein.

Alternatively, cutting mechanism 1350 may be an electrode coupled to control unit 1320. After a seal is completed, control unit 1320 transfers power from power source 1330 to cutting mechanism 1350 to electrically cut tissue. Cutting mechanism 1350 may also be a light source that emits a focused beam of light (i.e., a laser) to cut tissue. The light source may be a semiconductor laser or any other device that emits a focused beam of light.

Figure 14:
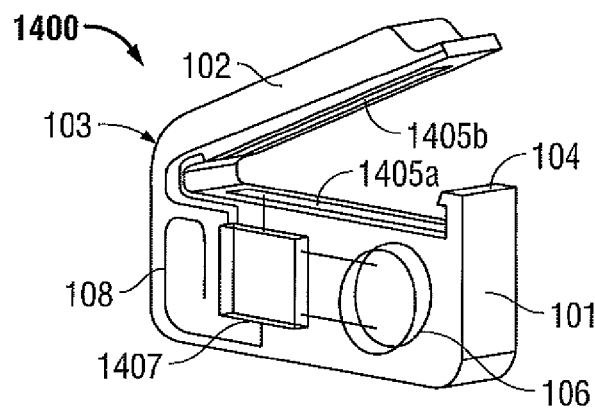
FIG. 14 is a schematic diagram of a tissue clip according to another embodiment of the present disclosure.
Figure 15:
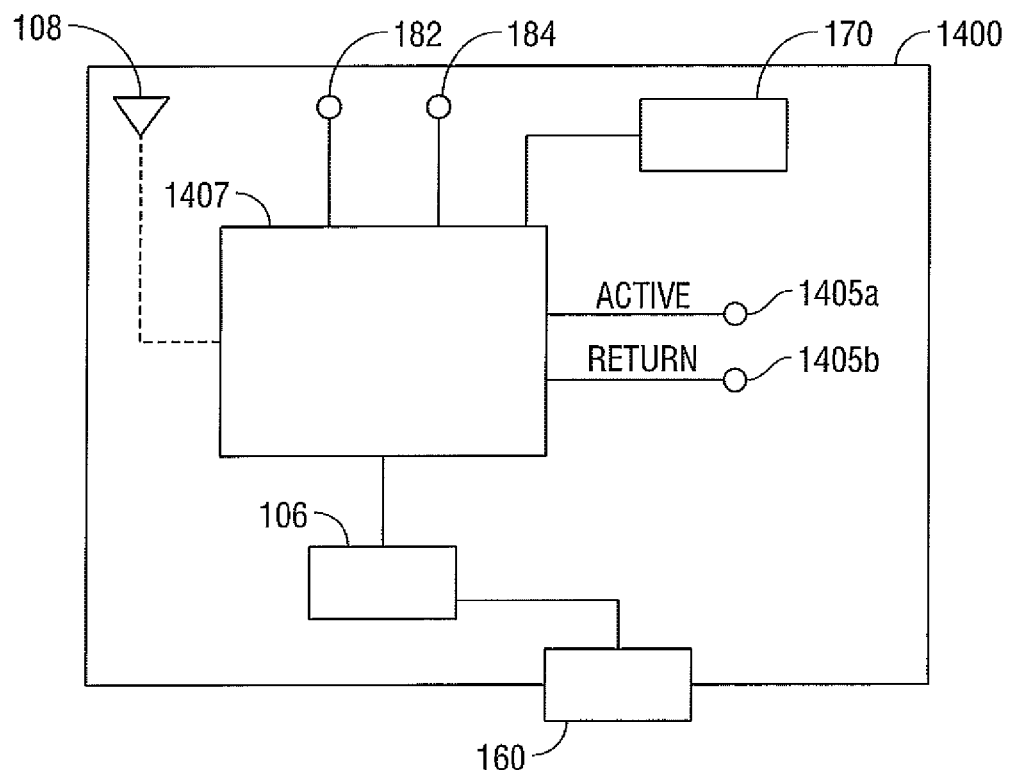
FIG. 15 is a system block diagram of the tissue clip of FIG. 14.

FIGS. 14 and 15 depict a tissue clip 1400 according to another embodiment of the present disclosure. As shown in FIGS. 14 and 15, tissue clip 1400 includes a control unit 1407 and an antenna array 1405. Control unit 1407 transfers energy from power source 106 to antenna array 1405 to apply microwave energy to tissue disposed between arm 102 and body 101. The microwave energy return to the control unit via return pad 1405b. As described above antenna 108 may receive instructions from an external control unit 202. Alternatively, control unit 1407 may include a memory and a processor. Memory may include a program or set of instructions that can be used to control the voltage output of control unit 1407. Tissue clip 1400 may also include any of the biasing members described above with regard to FIGS. 1B and 1C.

Figure 16:
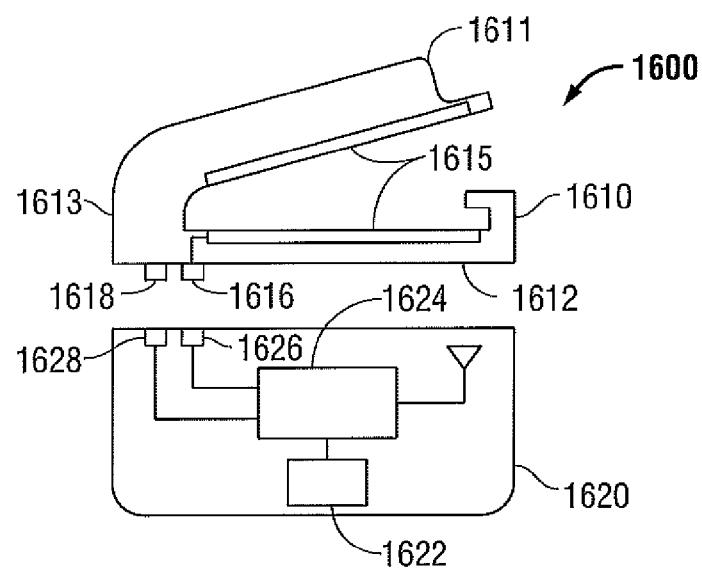
FIG. 16 is a schematic diagram of a tissue clip according to another embodiment of the present disclosure.

FIG. 16 depicts a tissue clip according to another embodiment of the present disclosure shown generally as 1600. Tissue clip 1600 includes an electrode assembly 1610 that is removably coupled to body 1620. Electrode assembly 1610 includes electrodes 1615 that are coupled to terminals 1616 and 1618. Electrodes 1615 are located on a pair of arms 1611 and 1612 that are coupled to each other via a flexible hinge 1613. Terminals 1616 and 1618 are removably coupled to terminals 1626 and 1628 of body 1620. Body 1620 includes a control unit 1624 and a power source 1622. Body 1620 and electrode assembly 1610 may include any of the features described hereinabove. Electrode assembly 1610 may be absorbable while body 1620 may be reusable by sterilizing body 1620 and coupling body 1620 to a different electrode assembly 1610. Tissue clip 1600 may also include any of the biasing members described above with regard to FIGS. 1B and 1C.

Figure 17:
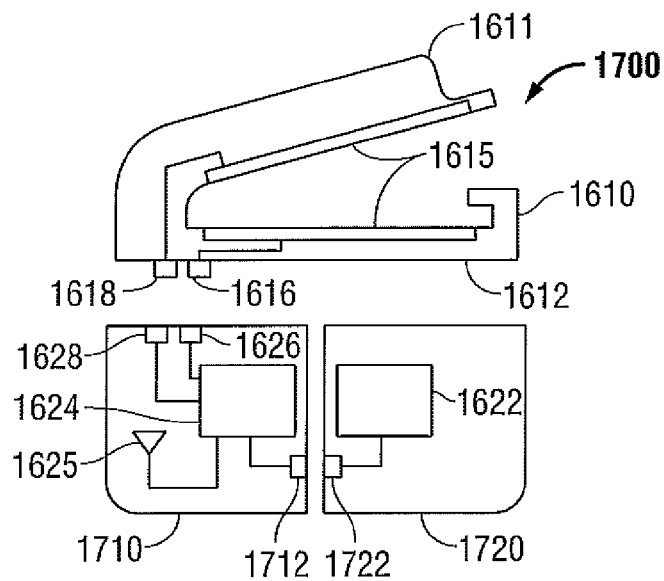
FIG. 17 is a schematic diagram of a tissue clip according to another embodiment of the present disclosure.

FIG. 17 depicts a tissue clip according to another embodiment of the present disclosure shown generally as 1700. Tissue clip 1700 includes an electrode assembly 1610 that is removably coupled to body 1710. Electrode assembly 1610 includes electrodes 1615 that are coupled to terminals 1616 and 1618. Electrodes 1615 are located on a pair of arms 1611 and 1612 that are coupled to each other via a flexible hinge 1613. Terminals 1616 and 1618 are removably coupled to terminals 1626 and 1628 of body 1710. Body 1710 includes a control unit 1624 and an antenna 1625. Body 1710 and electrode assembly 1610 may include any of the features described hereinabove. A battery pack 1720 is removably coupled to body 1710 by coupling terminal 1722 to terminal 1712. Battery pack 1720 includes a battery 1622 that may be a single use battery or a rechargeable battery. Electrode assembly 1610 may be absorbable while body 1710 and/or battery pack 1720 may be reusable by sterilizing body 1710 and/or battery pack 1720 and coupling body 1710 and/or battery pack 1720 to a different electrode assembly 1610. Tissue clip 1700 may also include any of the biasing members described above with regard to FIGS. 1B and 1C. Alternatively, electrode assembly may be coupled to a housing (not shown). The housing may be configured to receive body 1710 and/or battery pack 1720.

Figure 18A:
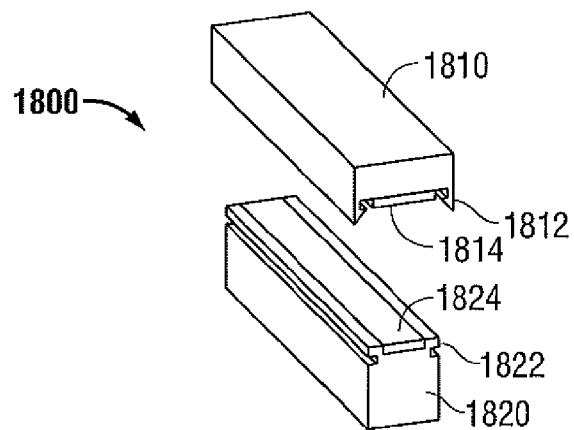
FIGS. 18A-18C are schematic diagrams of a tissue clip according to another embodiment of the present disclosure.
Figure 18B:
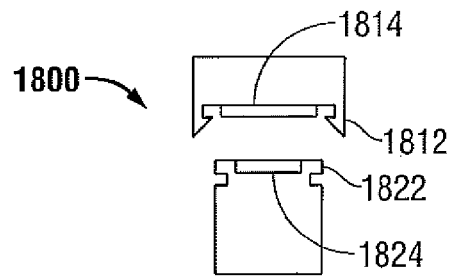
Figure 18C:
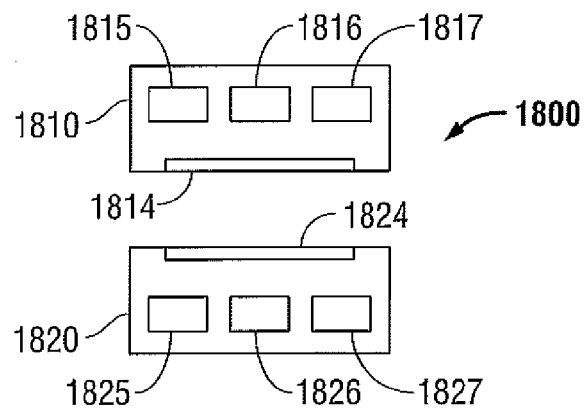

FIGS. 18A-18C depict a tissue clip 1800 according to another embodiment of the present disclosure. Tissue clip 1800 includes an arm 1810 that is removably coupled to body 1820. Arm 1810 includes an electrode 1814 and a retaining clip 1812. Body 1820 includes an electrode 1824 and a retaining lip 1822. Retaining clip 1812 and retaining lip 1822 are used to fix or selectively lock arm 1810 to body 1820 to grasp tissue disposed therebetween. Arm 1810 may include a power source 1815, control unit 1816 and sensor array 1817 similar to any of the power sources, control units and/or sensor arrays described above. Body 1820 may include a power source 1825, control unit 1826 and sensor array 1827 similar to any of the power sources, control units and/or sensor arrays described above.

Figure 19:
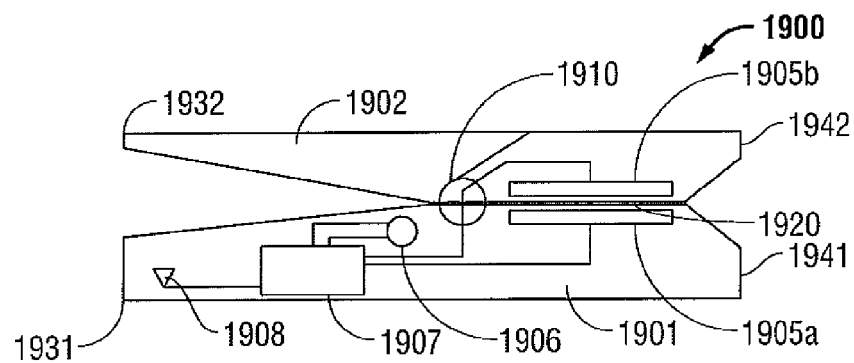
FIG. 19 is a schematic diagram of a tissue clip according to another embodiment of the present disclosure.

FIG. 19 depicts a tissue clip 1900 according to another embodiment of the present disclosure. Tissue clip 1900 includes a first arm 1901 and a second arm 1902 that are coupled together by a helical torsion spring 1910. First arm 1901 includes a power source 1906, control unit 1907, antenna 1908 and electrode 1905*a*. Second arm 1902 includes electrode 1905*b* Although FIG. 19 shows the power source 1906, control unit 1907, and antenna 1908 in first arm 1901, the power source 1906, control unit 1907, and antenna 1908 may be disposed in second arm 1902 or both the first arm 1901 and the second arm 1902. Power source 1906 is similar to the power sources described hereinabove. Control unit 1907 stores a program that, when executed, causes tissue clip 1900 to seal tissue grasped between distal ends 1941 and 1942 of first arm 1901 and second arm 1902, respectively. Antenna 1908 is configured to receive instructions from an external control unit or transmit information from a sensor (not shown) to an external control unit.

Tissue clip 1900 may be effective in emergency situations where access to hospitals is limited such as rural areas or combat situations. In operation, a user presses proximal ends 1931 and 1932 of first arm 1901 and second arm 1902, respectively, towards each other causing distal ends 1941 and 1942 to move away from each other. Tissue is placed between the distal ends 1941 and 1942 and then proximal ends 1931 and 1932 are released causing helical torsion spring 1920 to bias distal ends 1941 and 1941 toward each other to grasp tissue therebetween under the appropriate pressure to seal tissue. Stop members 1920 may be configured to extend from the electrode 1905*a* and/or 1905*b* a predetermined distance according to the specific material properties (e.g., compressive strength, thermal expansion, etc.) to yield a consistent and accurate gap distance during sealing. In some embodiments, the gap distance between the first arm 1901 and second arm 1902 during sealing ranges from about 0.001 inches to about 0.006 inches and, in one particularly useful embodiment, between about 0.002 and about 0.003 inches.

Helical torsion spring 1901 causes first arm 1901 and second arm 1902 to apply a sealing pressure to tissue grasped therebetween. In one embodiment, the sealing pressure is in the range of 3K g/cm$^2$ to 16 Kg/cm$^2$.

Figure 20A:
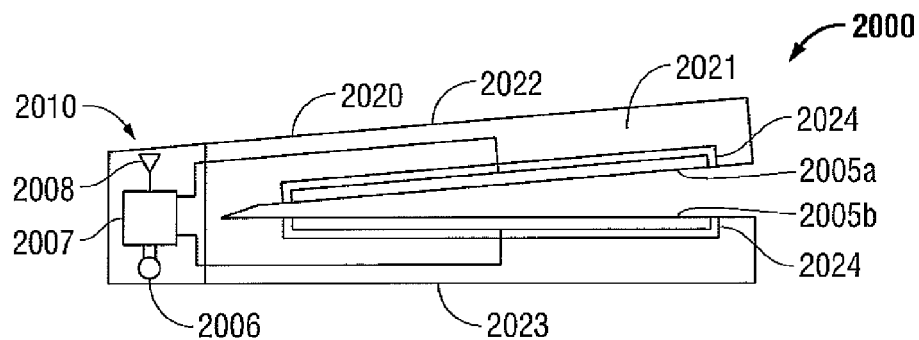
FIG. 20A is a schematic diagram of a tissue clip according to another embodiment of the present disclosure.

FIG. 20A depicts a tissue clip according to another embodiment of the present disclosure. As shown in FIG. 20A, tissue clip 2000 includes a control portion 2010 and a clip portion 2020. Control portion includes a power source 2006, control unit 2007, and antenna 2008. Power source 2006 is similar to the power sources described hereinabove. Control unit 2007 stores a program that, when executed, causes tissue clip 2000 to seal tissue grasped between arm 2022 and arm 2023. Antenna 2008 is configured to receive instructions from an external control unit or transmit information from a sensor (not shown) to an external control unit.

Clip portion 2020 may be made from a shape memory alloy 2021, e.g., copper-zinc-aluminum-nickel, copper-aluminum-nickel, and nickel-titanium (NiTi) alloys. Shape memory alloy 2021 may exhibit a one way effect or two-way effect. When outside the body, shape memory material is in an open shape with arm 2022 and arm 2023 spaced apart from each other. When tissue clip 2000 is placed inside a body, heat within the body causes clip portion 2020 to heat up past the austenitic start temperature ($A_s$) causing the shape memory alloy 2021 to change to its original shape where arm 2022 and arm 2023 are positioned relatively closer to each other to grasp tissue disposed therebetween.

Arm 2022 and arm 2023 include electrodes 2005*a* and 2005*b*, respectively. Electrodes 2005*a* and 2005*b* are disposed within insulators 2024 to electrically isolate electrodes 2005*a* and 2005*b* from shape memory alloy 2021. Insulator 2024 may be composed of any non-conductive material.

Arm 2022 and arm 2023 are configured to yield a consistent and accurate gap distance, which may range from 0.001 inches to about 0.006 inches, during sealing when clip portion 2020 is in its original shape. Further, arm 2022 and arm 2023 may apply a sealing pressure to tissue grasped therebetween when clip portion 2020 is placed in its original austenitic shape. In one embodiment, the sealing pressure is in the range of 3 Kg/cm$^2$ to 16 Kg/cm$^2$.

Although FIG. 20A depicts the control portion 2010 and clip portion 2020 as one unit, control portion 2010 may be removably coupled to clip portion 2020. Further, in some embodiments, control portion 2012 of tissue clip 2000 may only contain a power source 2006.

Figure 20B:
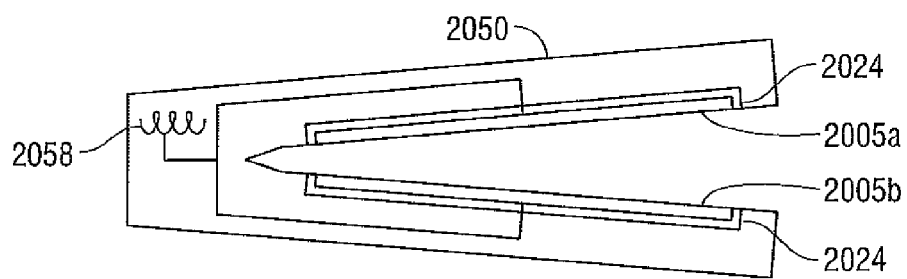
FIG. 20B is a schematic diagram of a tissue clip according to yet another embodiment of the present disclosure.

FIG. 20B depicts a tissue clip 2050 according to another embodiment of the present disclosure. Tissue clip 2050 is similar to clip portion 2020 described above. As depicted in FIG. 20B, tissue clip 2050 includes receiving coil 2058 that is configured to receive energy from an external control unit as will be described below with regard to FIG. 22.

Figure 21A:
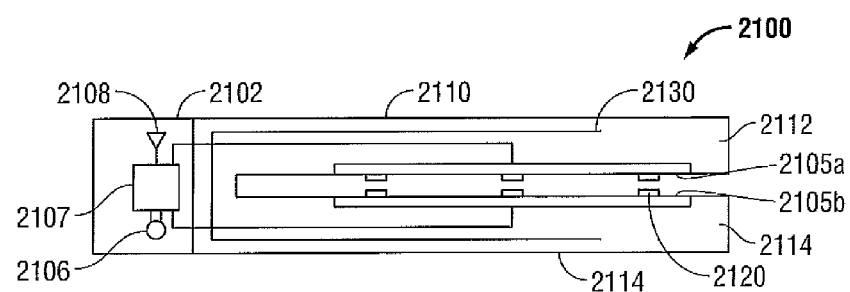
FIG. 21A is a schematic diagram of a tissue clip according to still another embodiment of the present disclosure.

FIG. 21A depicts a tissue clip according to another embodiment of the present disclosure. As shown in FIG. 21A, tissue clip 2100 includes a control portion 2102 and clip portion 2110. Control portion includes a power source 2106, control unit 2107, and antenna 2108. Power source 2106 is similar to the power sources described hereinabove. Control unit 2107 stores a program that, when executed, causes tissue clip 2100 to seal tissue grasped between arm 2112 and second arm 2114. Antenna 2108 is configured to receive instructions from an external control unit or transmit information from a sensor (not shown) to an external control unit.

Clip portion 2110 includes electrodes 2105a and 2105b that apply energy to tissue grasped between arms 2112 and 2114. A spring member 2130 is disposed in clip portion 2110 to bias arms 2112 and 2114 toward each other to grasp tissue therebetween. Arm 2112 and/or arm 2114 include stop members 2120 that are configured to yield a consistent and accurate gap distance, which may range from 0.001 inches to about 0.006 inches. Alternatively, spring member 2130 may be configured to achieve a desired gap between arm 2112 and arm 2114. Further, spring member 2130 may apply a sealing pressure to tissue grasped between arm 2112 and arm 2114. In one embodiment, the sealing pressure is in the range of 3 Kg/cm² to 16 Kg/cm².

Although FIG. 21A depicts the control portion 2102 and clip portion 2110 as one unit, control portion 2102 may be removably coupled to clip portion 2110. Further, in some embodiments, control portion 2102 of tissue clip 2100 may only contain a power source 2106.

Figure 21B:
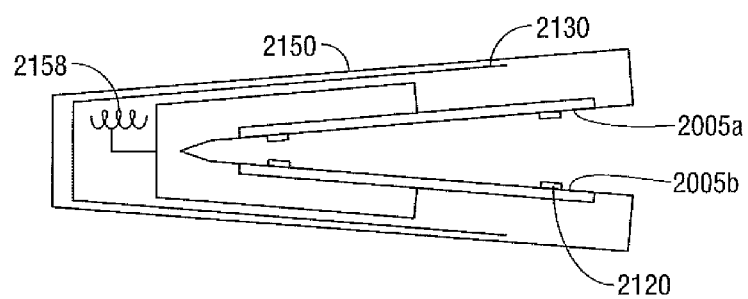
FIG. 21B is a schematic diagram of a tissue clip according to yet another embodiment of the present disclosure.

FIG. 21B depicts a tissue clip 2150 according to another embodiment of the present disclosure. Tissue clip 2150 is similar to clip portion 2110 described above. As depicted in FIG. 21B, tissue clip 2050 includes a receiving coil 2158 that is configured to receive energy from an external control unit as will be described below with regard to FIG. 22.

Figure 22:
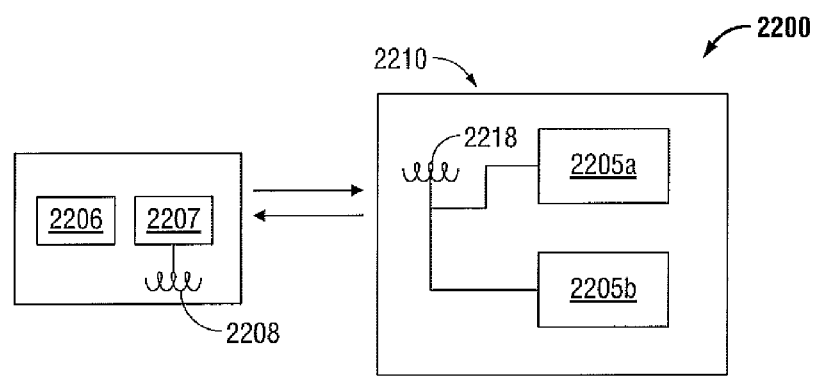
FIG. 22 is a system block diagram of a tissue sealing system according to another embodiment of the present disclosure.

FIG. 22 depicts a tissue clip system 2200 according to another embodiment of the present disclosure. Tissue clip system 2200 may use a power source placed outside of a tissue clip 2210 and the energy may be transferred from outside by excitation of an inductive current in a receiving coil placed inside the tissue clip. Different clips may have resonant receiving coils adjusted to different frequencies such that each clip can be supplied with power individually. The tissue clip may be controlled by varying the amplitude of the external electromagnetic field.

As shown in FIG. 22, tissue clip system 2200 includes a tissue clip 2210 and an external control unit 2220. Control unit 2220 includes a power source 2206, a control unit 2207, and transmitting coil 2208. Power source 2206 is similar to the power sources described hereinabove. Control unit 2207 stores a program that, when executed, causes tissue clip 2210 to seal tissue grasped between electrodes 2205a and 2205b. Transmitting coil 2208 generates an electromagnetic field that induces a current in receiving coil 2218. The inductive current generated by receiving coil 2218 is supplied to electrodes 2205a and 2205b to seal tissue grasped therebetween.

Although specific examples of tissue clips have been described above, any one of the above described tissue clips may include features from any of the other described tissue clips. For instance, the use of an external power source as described in FIG. 22 may be incorporated into any of the tissue clips described above.

As mentioned above, it is contemplated that the tissue clip embodiments described herein can use light, microwave, RF, or resistive energy to thermally treat tissue or seal tissue (as defined herein).

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figs. are presented only to demonstrate certain examples of the disclosure. Other elements, steps, methods and techniques that are insubstantially different from those described above and/or in the appended claims are also intended to be within the scope of the disclosure.

What is claimed is:

1. A tissue clip, comprising:
an arm having a first electrode and a proximal end portion;
a body having a proximal end portion pivotally coupled at the proximal end portion of the arm such that the arm is moveable from a first position relative to the body for approximating tissue and a second position closer to the body for grasping tissue therebetween, the body including:
a housing;
a power source disposed within the housing of the body; and
a second electrode coupled to the power source; and
a biasing member configured to generate an appropriate sealing pressure to tissue grasped between the arm and the body by biasing the arm relative to the body.

2. The tissue clip according to claim 1, further comprising a control unit configured to transfer energy from the power source to the first and/or second electrode.

3. The tissue clip according to claim 1, wherein the body includes an antenna configured to communicate with an external control unit.

4. The tissue clip according to claim 1, further comprising a sensor array configured to determine parameters of tissue between the arm and the body.

5. The tissue clip according to claim 1, wherein the first electrode and/or second electrode includes:
a stainless steel layer; and
a copper layer.

6. The tissue clip according to claim 1, wherein the first electrode and/or second electrode includes piezo electric sensors.

7. The tissue clip according to claim 1, wherein the first electrode includes:
an outer layer composed of a non-stick material; and
a flex circuit having a coil formed thereon.

8. The tissue clip according to claim 2, wherein the first electrode and second electrode cooperate with the control unit and the power source to seal tissue.

9. The tissue clip according to claim 8 further comprising a cutting element having an electrode configured to electrically cut tissue.

10. The tissue clip according to claim 9, wherein the cutting element cooperates with the control unit to cut tissue after the seal is completed.

11. The tissue clip according to claim 10, further comprising at least one sensor configured to sense the completed seal.

12. The tissue clip according to claim 11, wherein the control unit automatically activates the cutting element when the at least one sensor senses the completed seal.

13. The tissue clip according to claim 8, wherein the first electrode includes a first pair of tissue contacting surfaces and an insulator disposed therebetween and the second electrode includes:
- a second pair of tissue contacting surfaces;
- a pair of insulators disposed between the second pair of tissue contacting surfaces; and
- a cutting element disposed between the pair of insulators.

14. The tissue clip according to claim 13, wherein the cutting element includes an electrode that is configured to electrically cut tissue.

15. The tissue clip according to claim 9, wherein the cutting element is moveable to cut tissue after the formation of the tissue seal.

16. The tissue clip according to claim 1, wherein the first electrode of the arm is disposed distally of the proximal end portion of the arm.

17. The tissue clip according to claim 1, wherein the second electrode of the body is disposed distally of the proximal end portion of the body.

18. The tissue clip according to claim 2, wherein the control unit is disposed within the housing of the body.

19. The tissue clip according to claim 1, wherein the proximal end portion of the arm is connected to the proximal end portion of the body via a flexible joint.

* * * * *